United States Patent
Goeldner

(10) Patent No.: US 6,403,042 B1
(45) Date of Patent: Jun. 11, 2002

(54) DEVICE FOR STERILIZING CONTAMINATED MATERIALS

(76) Inventor: Helmut Goeldner, Gewerbegebiet Oehmer Feld, D-31633 Leese (DE)

(*) Notice: Subject to any disclaimer, the term of this patent is extended or adjusted under 35 U.S.C. 154(b) by 0 days.

(21) Appl. No.: 09/744,298
(22) PCT Filed: Jul. 20, 1999
(86) PCT No.: PCT/DE99/02211
§ 371 (c)(1), (2), (4) Date: Jan. 23, 2001
(87) PCT Pub. No.: WO00/04934
PCT Pub. Date: Feb. 3, 2000

(30) Foreign Application Priority Data

Jul. 23, 1998 (DE) .......................................... 198 33 023

(51) Int. Cl.[7] .......................... A61L 2/00; B65G 17/08; B65G 29/00; B01B 7/00; A23B 1/10
(52) U.S. Cl. ...................... 422/297; 422/308; 414/218; 198/612; 426/510; 426/520
(58) Field of Search ........................ 422/261, 268–269, 422/273–274, 284, 286–288, 295, 297, 305–309; 426/520, 521, 511, 510; 198/612; 414/218

(56) References Cited

U.S. PATENT DOCUMENTS 5,213,774 A * 5/1993 Noetzel
5,340,536 A * 8/1994 Datar et al.
5,425,925 A * 6/1995 Kline et al.
5,487,873 A * 1/1996 Bridges et al.

FOREIGN PATENT DOCUMENTS

DE 3938546 C2 11/1989
DE 19717839 A1 4/1997

* cited by examiner

Primary Examiner—Robert J. Warden, Sr.
Assistant Examiner—Monzer R. Chorbaji
(74) Attorney, Agent, or Firm—Crowell & Moring LLP

(57) ABSTRACT

An apparatus for disinfecting or sterilizing contaminated materials including a first worm screw (15) inside a pretreatment chamber (14) and a second worm screw (17) arranged close to the end of the first worm screw (15) and extending inside a treatment chamber (16). Elements are provided for sealing both ends of the treatment chamber (16) so that an elevated pressure can be maintained in the treatment chamber. Energy can be introduced into the treatment chamber in a controlled manner to supply or produce steam sufficient to create and maintain an elevated pressure and temperature needed to disinfect and/or sterilize the contaminated material. The pretreatment chamber (14) and the treatment chamber (16) are connected to each other by a reversing component (1) having two tube sections (2, 3) which form an angle relative to each other and which are secured to the pretreatment chamber (14) and the treatment chamber (16) by flanges (4, 5). The apparatus offers a high degree of flexibility with regard to mounting and modification of the angular position of the pretreatment and treatment chambers.

10 Claims, 2 Drawing Sheets

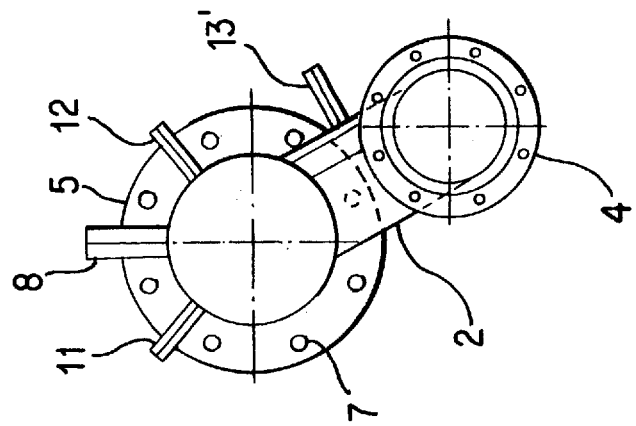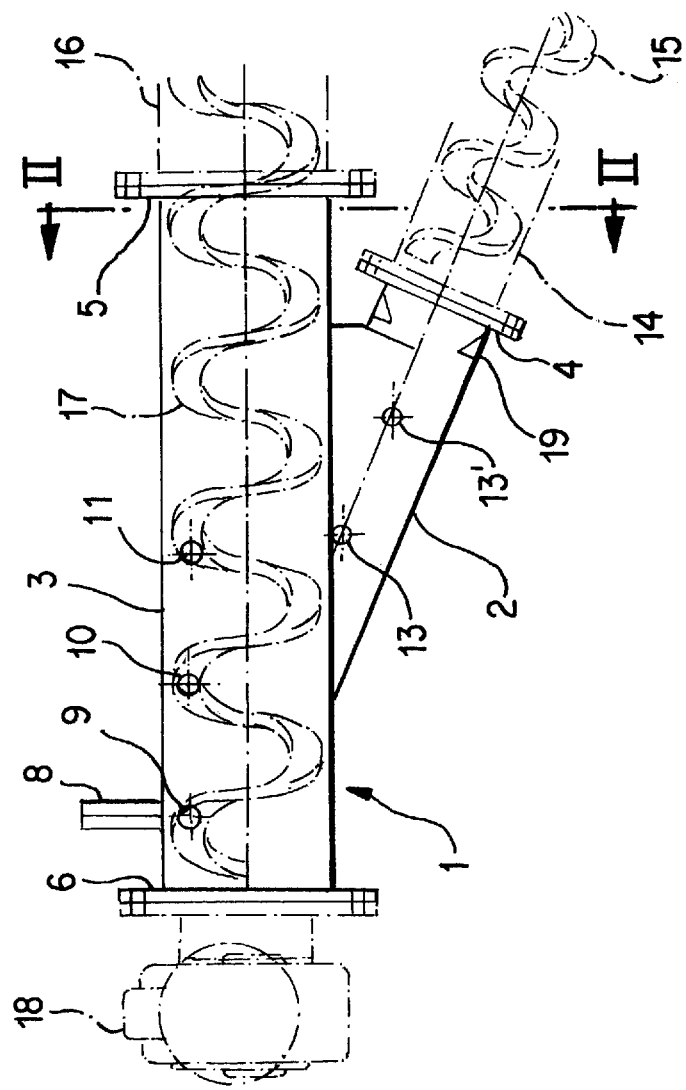

DEVICE FOR STERILIZING CONTAMINATED MATERIALS

BACKGROUND OF THE INVENTION

The invention relates to a device for disinfecting and/or sterilizing contaminated, in particular infected materials, having a first worm conveyor that runs inside a pretreatment chamber and a second worm conveyor that is mounted at the end of the first worm conveyor and runs inside a treatment chamber, wherein means are present for sealing the two end areas of the treatment chamber to build up elevated pressure. Energy can be introduced into the treatment chamber in a defined way, water vapor supplied and/or generated and an elevated pressure and the temperature necessary for disinfecting and/or sterilizing can be built up and maintained.

In the German patent application with the official file number 197 17 839.1-41, a high temperature disinfecting and/or high temperature sterilizing device is described which is especially suitable for hospital waste and in which the waste is supplied by way of a receiving hopper and a crusher with worm conveyors mounted in succession. The first worm conveyor runs inside a pretreatment chamber, wherein a heating of the material to be treated occurs in the pretreatment chamber. This first worm conveyor is mounted so that is inclined diagonally upward in its conveyor direction which safely assures that contaminated fluid that is introduced into the disposal hopper can only collect in the area below the disposal hopper and/or in a low-lying section of the worm conveyor.

The second worm conveyor is mounted on the end of the first worm conveyor and runs inside a treatment chamber that is arranged horizontally. The actual disinfecting and/or sterilizing process takes place inside the treatment chamber. To do this, means are provided for sealing the two end areas of the treatment chamber to build up an elevated pressure.

In this known device, the pretreatment chamber and the treatment chamber are connected to each other as a single unit. Thus, there are no assembly means present, by means of which the two chambers can be separated from each other in a simple way. This means that e.g. repair work involving the chambers can sometimes only be carried out with great effort.

The patent U.S. Pat. No. 3,464,342 already discloses a device for treatment of chicken feathers and the like having a first worm conveyor mounted inside a pretreatment chamber and a second conveyor that is mounted near the end of the first worm conveyor and runs inside a treatment chamber. The device has means for sealing the end of the treatment chamber, so that an elevated pressure is built up inside it. To do this, defined energy can be supplied by means of steam in order to provide the necessary pressure and the necessary temperature for removing moisture from the material that has been introduced into the apparatus. The pretreatment chamber and the treatment chamber are connected to each other at an angle by a reversing component which is fastened by means of a flange connection so that it can be disconnected on one side to the end section of the pretreatment chamber and on the other side to a connecting pipe that opens vertically into the treatment chamber.

SUMMARY OF THE INVENTION

It is therefore the object of the invention to provide a device of this general type for treatment of contaminated, and in particular infected, materials that offers great flexibility with respect to its installation capability and with respect to the ability to change the angular position of the pretreatment chamber and the treatment chamber to each other.

The object is achieved by a device of this general type, in which the second worm conveyor basically extends inside the entire area of the associated tube section.

Because of this, it is possible to separate the pretreatment chamber and the treatment chamber from each other by simple disassembly of the reversing component. This makes it easier, for example, to replace one of the two worm conveyors.

In addition, the inclination of the pretreatment chamber can be changed easily by replacing the reversing component with a reversing component in which the two tube sections are arranged at a different angle to each other. This can occur, for example, in order to optimize the area within the pretreatment chamber in which fluid collects. In addition, by simply using an appropriate reversing component, the transition surface of the two tube sections is easy to change. Another advantage is that if there is wear on the reversing components, the pretreatment tube does not have to be changed and vice versa.

Preferably, the two tube sections of the reversing component are straight in longitudinal direction. In this case, for example, the second worm conveyor that is mounted in the treatment chamber can also extend into the corresponding tube section of the reversing component. This tube section can have another flange that is located at the end of the tube section lying opposite the first flange. On this other flange, e.g. a drive for the second worm conveyor can be mounted.

The reversing component can have an inlet neck for samples. In addition, connecting nipples for measuring sensors can also be provided on the reversing component, in order to measure the temperature, the pressure, the moisture content or the fill level in the treatment chamber, for example.

A preferred angle range of the reversing component lies between 20° and 45°. This angle approximately corresponds to the angle at which the pretreatment chamber is tilted upward in the conveyor device, since the treatment chamber is preferably mounted so that it is horizontal.

Preferably means for sealing the treatment chamber are mounted inside the reversing component. Because of the simple replacement capability of the reversing component, the sealing means can also be changed in a simple manner. This permits great flexibility in the use of the device. Therefore, for example, a cone-shaped ring can be mounted in the end area of the first worm conveyor inside the reversing component in such a way that the material is compressed.

The first worm conveyor is preferably surrounded with a heating element in order to heat up the material to be treated while it is being conveyed by the worm.

BRIEF DESCRIPTION OF THE DRAWINGS

In the following, the invention will be explained in further detail with respect to an embodiment of the apparatus according to the invention, with reference being made to the figures, which show:

FIG. 1, a schematic side view of a reversing component according to the invention that is connected with a pretreatment chamber and a treatment chamber that are only indicated and not shown in detail.

FIG. 2, a schematic top view of the reversing component according to FIG. 1;

DETAILED DESCRIPTION OF PREFERRED EMBODIMENTS

Figure 3:
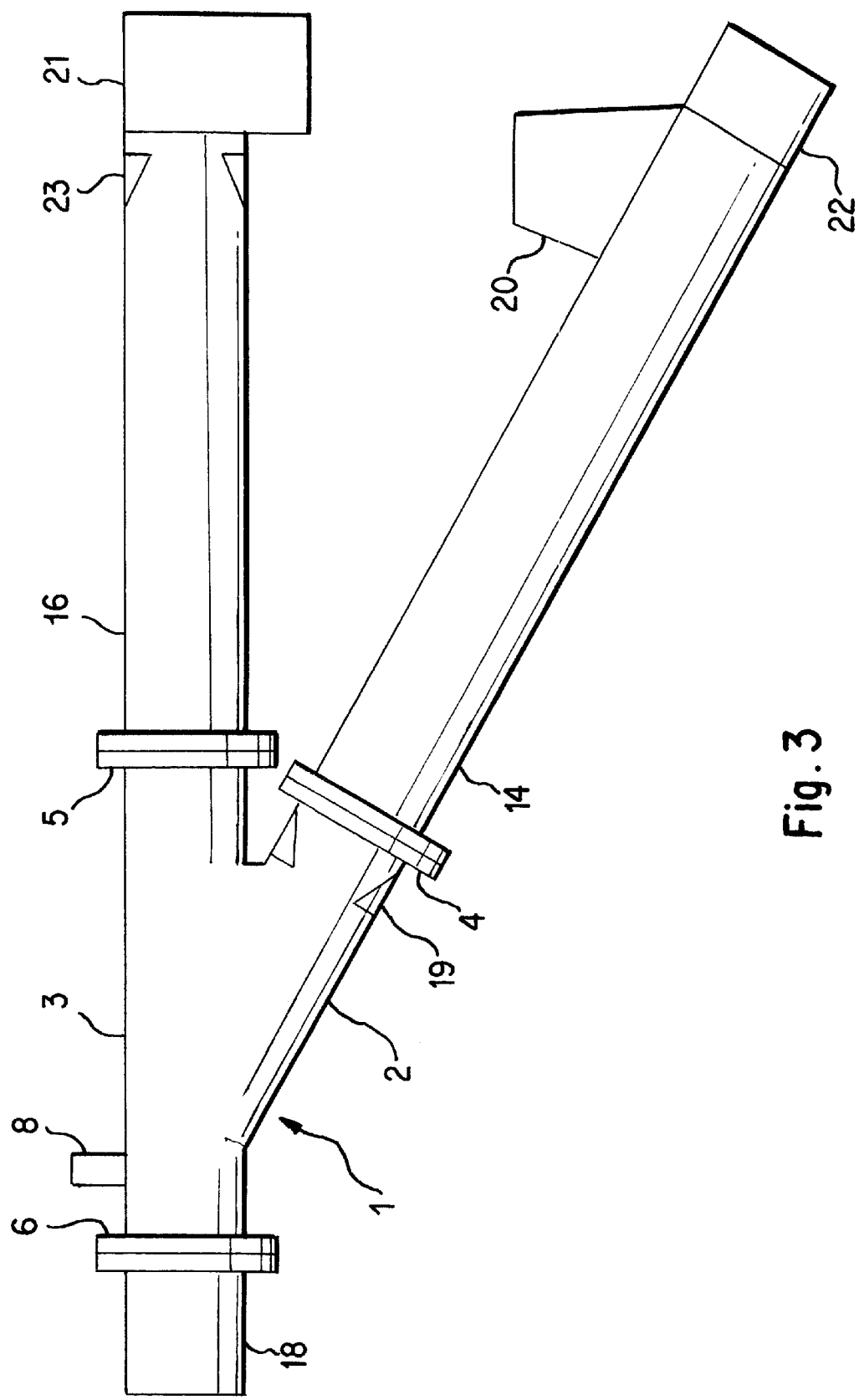
FIG. 3, a schematic general representation of the device according to the invention having the reversing component according to FIG. 1.

FIG. 1 shows a reversing component 1, that has two tube sections 2 and 3. The two tube sections 2 and 3 are connected to each other so that they can communicate. On its free end, tube section 2 has a flange 4. On each of its two ends, tube section 3 has a flange 5 or 6. These flanges 4, 5 and 6 have openings, e.g. indicated with 7 (FIG. 2) so that they can be screwed together.

Tube section 3 is provided with a tube 8 to input samples. In addition, in longitudinal direction on both sides, tube section 3 has thee connecting pieces for connection of measuring sensors, of which connecting pieces 9, 10, 11 and 12 are shown in FIG. 1 and FIG. 2. Tube section 2 has two other connecting pieces 13 and 13' for connecting measuring sensors.

The reversing component 1 also has a cone-shaped ring 19 that reduces the free passage cross section of tube section 2 in conveyor direction.

Other components of a device according to the invention are shown in FIG. 1 in dotted lines. This involves a pretreatment chamber 14 that is only partially shown, to which tube section 2 is mounted by way of flange 4. A first worm conveyor 15 is located in pretreatment chamber 14, which can also extend in, up to the transition piece.

Tube section 3 is fastened to a treatment chamber 16 by flange 5. A second worm conveyor 17 runs inside treatment chamber 16 and tube section 3. The second worm conveyor 17 is moved by drive 18 that is fastened to tube section 3 by means of flange 6.

FIG. 3 shows the device schematically in an overall representation. In particular, this diagram shows an input unit 20 with a crusher that is not shown and an ejector 21 and a drive 22 of the first worm conveyor 15. In addition, another cone-shaped ring 23 is shown, that is mounted on the output side within treatment chamber 16.

The embodiment of the invention shown in the figures is designed to function in the following manner.

Contaminated material is supplied by way of inlet unit 20 to the first worm conveyor 15, which extends inside pretreatment chamber 14. Worm conveyor 15 is surrounded by a heating element (not shown) so that the material to be treated is heated in a defined manner while it is being conveyed by worm conveyor 15. In addition, a compression of the material also takes place in worm conveyor 15 such that a sealing material plug is created in its end area. This occurs on one hand because of the fact that the pitch angle of worm conveyor 15 is reduced in its end area. On the other hand, the compression is achieved by a cone-shaped ring 19.

Worm conveyor 15 transports the material to the second worm conveyor 17 which extends essentially inside the treatment chamber 16, but also inside tube section 3. A stress relief and loosening of the structure of the material to be treated takes place inside treatment chamber 16. The second worm conveyor 17 is also surrounded by a heating element and is designed for actually treating the material. Energy can be introduced in pulses into treatment chamber 16, in addition steam can be introduced and/or generated and an elevated pressure built up and maintained for the temperature necessary for disinfecting and/or sterilizing. In turn, worm conveyor 17 compresses the material in its end area to a second sealing plug of material due to the decreased pitch of worm 17 and by means of the cone-shaped ring 23. Because of this, the elevated pressure required for disinfecting and/or sterilizing can be maintained for a defined period of time between the two material plugs of worm conveyors 15, 17, which act as seals.

Since the first worm conveyor 15 is mounted at an angle of approx. 30° to the horizontal plane, a forward conveyance of the material results. This very securely prevents contaminated fluid from flowing unnoticed out of the area below the input unit into the system, and the process from occurring without treatment and/or with insufficient treatment.

Because of the fact that reversing component 1 can be easily replaced, various parameters of the device according to the invention can be modified in a simple manner. This includes, e.g. the pitch of first worm conveyor 15 and the means 19 in reversing component 1 for sealing treatment chamber 16. With the device according to the invention, contaminated materials, preferably hospital waste, but also, for example, clarifier sludge, contaminated earth, as well as foodstuffs such as grains and spices can be treated, safely disinfected and even sterilized depending on requirements and on the system layout.

What is claimed is:

1. An apparatus for disinfecting or sterilizing contaminated material comprising a pretreatment chamber, a first worm conveyor inside the pretreatment chamber, a treatment chamber, and a second worm conveyor mounted adjacent a discharge end of the first worm conveyor and extending through the treatment chamber, means for sealing end areas of the treatment chamber to enable an elevated pressure to be maintained in the treatment chamber, and means for controlled introduction of energy into the treatment chamber in order to supply or generate steam and build up an elevated pressure and temperature needed for disinfection or sterilization of the contaminated material, wherein the pretreatment chamber and treatment chamber are connected to each other by a reversing component comprising two tube sections arranged at an angle to each other, respective tube sections of said reversing component being releasably mounted to the treatment chamber and to the pretreatment chamber by flanges so that the reversing component can be disconnected, and wherein the second worm conveyor extends inside essentially the entire area of the respective reversing component tube section connected to the treatment chamber.

2. An apparatus according to claim 1, wherein the two tube sections of the reversing component are each linear tubes.

3. An apparatus according to claim 1, wherein tube section connected by a flange to the treatment chamber has a second flange at an end opposite the flange which connects the tube section to the treatment chamber.

4. An apparatus according to claim 3, further comprising a drive mounted on said second flange for driving said second worm conveyor.

5. An apparatus according to claim 1, further comprising an inlet nipple on said reversing component for introducing for samples into the treatment chamber.

6. An apparatus according to claim 1, further comprising at least one connecting nipple on said reversing component, each connecting nipple receiving a measuring sensor for measuring at least one parameter selected from the group consisting of the temperature, the pressure, the moisture level and the fill level in the reversing component.

7. An apparatus according to claim 1, wherein the two tube sections of the reversing component form an angle of from 20° to 45° with each other.

8. An apparatus according to claim 7, wherein the treatment chamber is at least substantially horizontal and the pretreatment chamber is inclined diagonally upward in the conveying direction of said first worm conveyor.

9. An apparatus according to claim 1, wherein said sealing means comprise means mounted inside the reversing component for sealing the treatment chamber.

10. An apparatus according to claim 9, wherein the sealing means comprise a cone-shaped ring mounted adjacent a discharge end of the first worm conveyor such that a compressed plug of contaminated material to be treated is formed adjacent said ring.

* * * * *